United States Patent [19]

Chien et al.

[11] Patent Number: 4,906,169

[45] Date of Patent: Mar. 6, 1990

[54] TRANSDERMAL ESTROGEN/PROGESTIN DOSAGE UNIT, SYSTEM AND PROCESS

[75] Inventors: Yie W. Chien, North Brunswick; Te-Yen Chien; Yih-Chain Huang, both of Piscataway, all of N.J.

[73] Assignee: Rutgers, The State University of New Jersey, New Brunswick, N.J.

[21] Appl. No.: 131,462

[22] Filed: Dec. 16, 1988

Related U.S. Application Data

[63] Continuation-in-part of Ser. No. 947,130, Dec. 29, 1986, abandoned.

[51] Int. Cl.⁴ ............................................. A61F 13/02
[52] U.S. Cl. ................................. 424/448; 424/449; 424/447
[58] Field of Search ................................ 424/448, 449

[56] References Cited

U.S. PATENT DOCUMENTS

| | | | |
|---|---|---|---|
| 3,996,934 | 12/1962 | Affaroni | 128/268 |
| 4,031,894 | 6/1977 | Urqwhart | 128/268 |
| 4,286,592 | 9/1981 | Chandrasekaram | 128/260 |
| 4,321,252 | 3/1982 | Keith | 424/28 |
| 4,336,243 | 6/1982 | Sandvordecker | 424/449 |
| 4,615,699 | 10/1986 | Gale et al. | 424/449 |
| 4,624,665 | 11/1986 | Nuwayser | 424/449 |
| 4,687,481 | 8/1987 | Nawayser | 424/449 |

Primary Examiner—Ellis P. Robinson
Assistant Examiner—Leon Horne
Attorney, Agent, or Firm—Leroy G. Sinn

[57] ABSTRACT

Transdermal estrogen/progestin absorption dosage unit have been developed which comprise a backing layer, an adjoining polymer layer is an adhesive layer in which at least minimum effective dose of an estrogen is dissolved or microdispersed. Adhered to the polymer layer in an adhesive layer in which is dissolved and/or microdispersed at least minimum doses of progestin. Presently preferred is use of the natural estrogen, 17-beta-estradiol, or ethinyl estradiol or combinations thereof and of the progestin, norethindrone or norgestimate or combinations thereof. The units have biologically acceptable adhesive and polymer layers. The adhesive layer can have dispersed one or more skin permeation enhancing agents. A separating layer can optionally be used in making the dosage units, which separate space the adhesive and polymer layers, which permits estrogen tansmission from the polymer layer during treatment. Dosage units are provided which transdermally deliver at least minimum daily doses of the estrogen and progestin for multiple days, such as for one week. The invention also provides a process of fertility control and estrogen replacement therapy using the novel dosage units. Also, the invention provides a fertility control system for fertility control using the novel dosage units.

23 Claims, 5 Drawing Sheets

TRANSDERMAL ESTROGEN/PROGESTIN DOSAGE UNIT, SYSTEM AND PROCESS

CROSS-REFERENCE TO RELATED APPLICATION

This application is a continuation-in-part of U.S. application Ser. No. 947,130, filed December 29, 1986, now abandoned.,

TECHNICAL FIELD

This invention relates to a novel transdermal fertility control system and a process for controlling fertility. The system involves transdermal estrogen/progestin absorption dosage units adapted for adhesion to the female subject desiring fertility control or prevention of an unwanted pregnancy. Additionally, the invention relates to a method of controlling fertility by utilizing a transdermal system of applying a series of transdermal estrogen/progestin dosage units having a polymer layer adhered to a backing layer and an adhesive layer adhered to the polymer layer, said polymer and adhesive layer having dissolved and/or microdispersed therein estrogen and progestin, respectively, in effective dosage amounts. Preferably, the estrogen used is beta-estradiol or ethinyl estradiol and the progestin used is norethindrone or norgestimate. The dosage units can also be used in estrogenic replacement therapy.

BACKGROUND ART

Estrogenic therapies include two main areas, fertility control and estrogenic replacement.

Fertility has been controlled by use of a number of orally administered hormone products. The products are ordinarily a combination of an estrogen and a progestin. A synthetic estrogen is ordinarily used as the estrogen component since the natural estrogen, 17-beta-estradiol, is almost completely destroyed, usually by over 90 percent, when taken orally. It is destroyed to a degree in the digestive tract before it is absorbed but primarily the destructive metabolism of 17-beta-estradiol occurs during the first pass hepatic metabolism. Since such a large amount is destroyed, in order to provide an effective dosage orally, a large excess must be administered with uncertain effectiveness and a large amount of unwanted metabolic products. Therefore, a synthetic estrogen such as ethinyl estradiol normally is orally administered with less than desired results.

The progestin component generally inhibits, as intended, ovulation. Also, in the case of administered progestin, a substantial amount of metabolic breakdown occurs causing undesired metabolic products with undesired effects.

Therefore, in the oral administration of what is commonly referred to as "the pill" or other orally administered products, considerably overdosing is necessary to obtain a high degree of assurance that the desired fertility control will be obtained.

A number of major side effects have reportedly been associated with the administration of oral fertility control preparations, such as thrombophlebitis and thrombosis, pulmonary embolism, coronary thrombosis, myocardial infarction, cerebral thrombosis, cerebral hemorrhage and hypertension. These side effects have been attributed to the estrogen component in the oral preparations. Use of the progestin-only preparations (mini-pill) has been found to eliminate the side effects of estrogen. However, the fertility control is less than that of the combined preparations and the menstrual cycle also becomes more irregular. It has been reported that less incidence of irregular bleeding is observed if the progestin is administered at a more constant rate of delivery. Besides the side effects, the oral fertility control preparations also have the disadvantage of fertility control efficacy depending highly on the degree of patient compliance. The risk of pregnancy is known to increase with each pill missed.

An ideal and patient-acceptable fertility control system should provide the following advantages: minimized side effect, increased ease of administration, rapid termination of treatment, if needed, and improved patient compliance. In recent years, considerable attention has already been directed to the development of implantable, intrauterine, intracervical or intravaginal fertility control delivery systems to provide a prolonged and controlled administration of steroidal hormones to the body for achieving fertility control; however, none of the delivery systems developed so far can be considered as ideal and side effect-free.

Other fertility control means have been used, such as topical creams and intravaginal devices, which deliver combinations of one or more progestins and one or more estrogens, including the naturally-occurring estrogen, 17-beta-estradiol. However, the undersirable aspects of such fertility control systems are evident.

It is, therefore, highly desired that transdermal systems be provided which permit (1) use of the natural estrogen, 17-beta-estradiol, if desired, (2) use of a minimum number of dosage units for each menstrual cycle, such as use of three successive weekly dosage units, and (3) adherence to the skin of the subject which would administer sufficiently high levels of estrogen and progestin hormones to provide high assurance of fertility control without a high amount of undesired metabolic or chemical degradative products. Development of a rate-control transdermal drug delivery system, which is capable of minimizing any individual variability and regional differences in skin permeability, is a necessity to attain a predictable blood level of a drug. The transdermal rate-control drug administration is known to offer several potential advantages for systemic medication: (i) avoidance of the risk and inconvenience of intravenous therapy and of the variability in absorption and metabolism associated with oral therapy; (ii) continuity of drug administration, permitting the use of a pharmacologically-active agent with short biological half-life; (iii) efficacy can be achieved with lower total daily dosage of drug, because of reduced hepatic first-pass metabolism and continuous drug input; (iv) less chance of over- or under-dosing, as a result of prolonged, programmed delivery of drug at required therapeutic rate; (v) provision of a simplified medication regimen; and (vi) ability to rapidly terminate the drug infusion, if needed, by removal of the drug delivery system from skin surface. Therefore, a transdermal contraceptive delivery system, which is capable of providing on a fast effective basis dual-delivery of an estrogen and a progestin at controlled rates for a specific duration would be an ideal system for achieving fertility regulation in women.

The second main area of estrogenic therapy concerns the need for estradiol replacement therapy. It is caused by menopause (the cessation of ovarian function), oophorectomy (loss of one or both ovaries by surgery) or by pituitary failure. Replacement estrogenic therapy is an important need. Besides the need to alleviate the menopausal symptoms caused by estrogenic steroid deficiency, there are additional contributions of such replacement estrogenic therapy associated with osteoporosis (loss of bone mass) and atherosclerosis. It has been found advantageous to administer also an amount of progestin as a part of such estrogenic replacement therapy. There is clearly a need for improvements in means and methods for estrogenic steroid therapy. Even though it has been found that estradiol itself or estradiol in the form of certain derivatives such as nonoor diesters (e.g., acetate esters) can be absorbed transdermally, it is desired that improved transdermal estradiol and other estrogenic steroid absorption dosage unit forms and processes of transdermal administration be developed.

SUMMARY OF INVENTION

Provided by this invention is a transdermal fertility control absorption system which permits fertility control by using sequentially three transdermal adhesive dosage units which can easily be applied to a selected skin area.

The first patch ordinarily is applied on the fifth day of a menstrual cycle. The dosage unit is replaced by the second unit after 7 days and the second is replaced by a third at the end of another 7 days. Then, at the beginning of the next menstrual cycle, another sequential course of 3 fertility control patches is again used, which course is repeated again and again as long as desired.

The transdermal estrogen/progestin dosage units of this invention comprise:

(a) a backing layer which is substantially impervious to the estrogen and progestin hormones to be delivered transdermally and which optionally is breathable, especially if the dosage unit is used on a long-term basis, such as for several days;

(b) a polymer layer which is in contact with said backing layer and which has dissolved and/or microdispersed therein an effective amount of an estrogen, preferably 17-beta-estradiol, ethynyl estradiol, or combinations thereof, said polymer layer providing a dosage amount of the estrogen to be delivered transdermally; and (c) an adhesive layer which can adhere the dosage unit in intimate contact with the skin of the subject being treated to permit the hormones to be absorbed transdermally, said adhesive layer being adhered to the polymer layer and having dissolved and/or microdispersed therein an effective dosage amount of a progestin, preferably norethindrone, norgestimate or combinations thereof, said adhesive layer being bioacceptable and permitting said progestin and said estrogen to be transmitted for transdermal absorption, said adhesive layer having an effective amount of a skin absorption enhancing agent.

Optionally, another layer can be included in the dosage units between the polymer layer (b) which has present an estrogen and the adhesive layer (c) which has present a progestin. In this separating layer, it is preferable to have present little or no estrogen or progestin. The separating layer can be made of adhesive polymers such as used in making adhesive layer (c), with a bioacceptable polyisobutylene which permits the estrogen in layer (b) to be transmitted for transdermal absorption being presently preferred. Additionally, it is presently preferred that the separating layer be free of any substantial amount of skin absorption enhancing agent.

The estrogen dissolved or microdispersed in the polymer layer comprises an amount of 17-beta-estradiol or ethinyl estradiol effective in providing the role of estrogen in fertility control or in estrogen replacement and norethin-drone or norgestimate dissolved or microdispersed in the adhesive layer comprises an amount which will provide the role of progestin in the desired fertility control system or in estrogen replacement. Desirably, the dosage units will provide the desired rate of transdermal absorption of the estrogen and progestin components for a period of several days, preferably for one week. Use of week-long transdermal dosage units minimize the possibility of missed administration of a dosage in fertility control.

The backing layer is made from materials that are substantially impermeable with regard to the hormones of the transdermal dosage unit. It can be made of polymers such as polyethylene, polypropylene, polyurethane, polyvinyl-chloride, polyesters such as poly(ethylene phthalate), and foils such as laminates of polymer films with metallic foils such as aluminum foil. If the dosage units are used on a long term basis, such as for a multiple of days, the backing preferably has a microporosity to permit passage of sweat and air to minimize any skin hydration.

The polymer disc layer is suitably fabricated from biologically acceptable lipophilic or hydrophilic polymers, which will permit the estrogen to be transmitted for transdermal absorption and which provide compatibility and stability for the estrogen. The polymer layer which has the estrogen distributed therein can preferably be made of a suitable polymeric adhesive, such as a suitable polyacrylic or a silicone adhesive in which the estrogen is stable and microdispersible or soluble. The polymer layer can also be made using a polymer to fabricate a disc in which the estrogen is microdispersed. The polymer-estrogen mixture is then formed into a layer of an appropriate thickness and suitable surface area and is cured, if desired. The polymer disc layer is then adhered to the backing layer. Care must be taken that the polymer selected is compatible with the pharmaceutical, permits its release for transdermal absorption and is free or sufficiently free from any biologically unacceptable components.

Other estrogenic steroid hormones can be used in partial or complete replacement of 17-beta-estradiol, for example, an ester of 17-beta estradiol which is biologically compatible and can be effectively absorbed transdermally and at a rate compatible with the rate of absorption of progestin. Also, it is ordinarily desired that such esters are bioconvertible by components of the skin or other portions of the body, such as hydrolytical enzymes (e.g., esterase), to 17-beta-estradiol. If the derivative is an ester, the derivative can be selected from mono- or di-esters since estradiol has hydroxy groups at the 3- and 17-positions, the 3-mono and 17-mono as well as the 3,17 di-esters can be made by generally known esterification methods. Some ester derivatives will be absorbed more readily than the basic 17-beta-estradiol. In selection of ester derivatives, it is ordinarily preferred that the main estrogen hormone used be absorbed at a rate to provide a desirable amount of the estrogen hormone component on a daily basis in a system which simultaneously effects transdermal absorption of the progestin hormone in an effective daily dosage amount over a several day period, preferably one week.

Regarding the daily dosages of progestin, about 100 to about 1500 mcg, preferably about 125 to about 250 mcg/day if the progestin used is norgestimate and about 1000 mcg/day is generally satisfactory if the progestin is norethindrone. Regarding estrogen, about 25 to about 50 mcg/day of estrogen based on 17-beta-estradiol are presently believed desired daily doses for humans.

Finally, the adhesive layer of the dosage unit is assembled with the other layer elements to form the dosage unit. The adhesive layer selected can vary depending on many factors including economic factors such as the type of manufacturing equipment most readily available, the rapidity of absorption desired or other factors. For example, the adhesive layer can be applied directly to the polymer layer. A skin permeation enhancer compound can be mixed thoroughly with the adhesive polymer which is suitable for adhesion to the skin locus to which the transdermal dosage unit will be applied. The progestin used is also dissolved or microdispersed in the adhesive layer. The adhesive layer can be applied to the polymer layer by spraying or by solvent casting or laminating. The concentration of skin permeation enhancer compound, if employed, can be reduced in the portion of the adhesive layer means coming in contact with the subject to be treated, especially if less than desired adhesion is realized in the adhesive layer, by applying the surface portion of the adhesive layer separately, wherein the adhesive composition has a lower concentration of skin permeation enhancer compound or progestin or both. The adhesive layer is desirably thin in the micron-range thickness, suitably 5-200 microns in thickness, desirably about 10 to 180 microns, and preferably about 20 to 150 microns in thickness. Also, if desired, an additional adhesive means can be used in the form of a ring adhered to the backing layer which extends beyond the circumference of the polymer layer.

The optional separating layer if empoyed is applied to the polymer layer prior to the assembly of the adhesive layer (c) having present progestin. Alternatively, the separating layer can be applied to the surface of the adhesive layer prior to its assembly into the dosage unit. The separating layer is suitably made of a suitably polyisobutylene.

The absorption rate of one or both of the hormones of the transdermal hormone absorption dosage units of the invention can be increased, such as by having an Enhancing Factor of at least 1.2, preferably at least 1.3, and more preferably at least about 1.5 or 2.0. Enhancing Factor is defined as the ratio of normalized permeation rate [in mcg/cm$^2$/hr] of a dosage unit of this invention with skin permeation enhancer/the normalized permeation rate of a corresponding dosage unit without enhancer.

The invention also is a process for administering said hormones transdermally by forming hormone-containing dosage units having a polymer layer which has the estrogen dosage dissolved or dispersed therein, to which polymer layer is adhered a backing layer, said dosage unit having assembled therewith an adhesive layer, which transports the estrogen and progestin and contains the progestin and transdermal absorption enhancing agent; applying the dosage unit in intimate contact with the skin of the subject treated; and administering the hormones transdermally to said subject to achieve fertility control or estrogen replacement.

DETAILED DESCRIPTION OF THE INVENTION AND THE PREFERRED EMBODIMENTS

Figure 1:
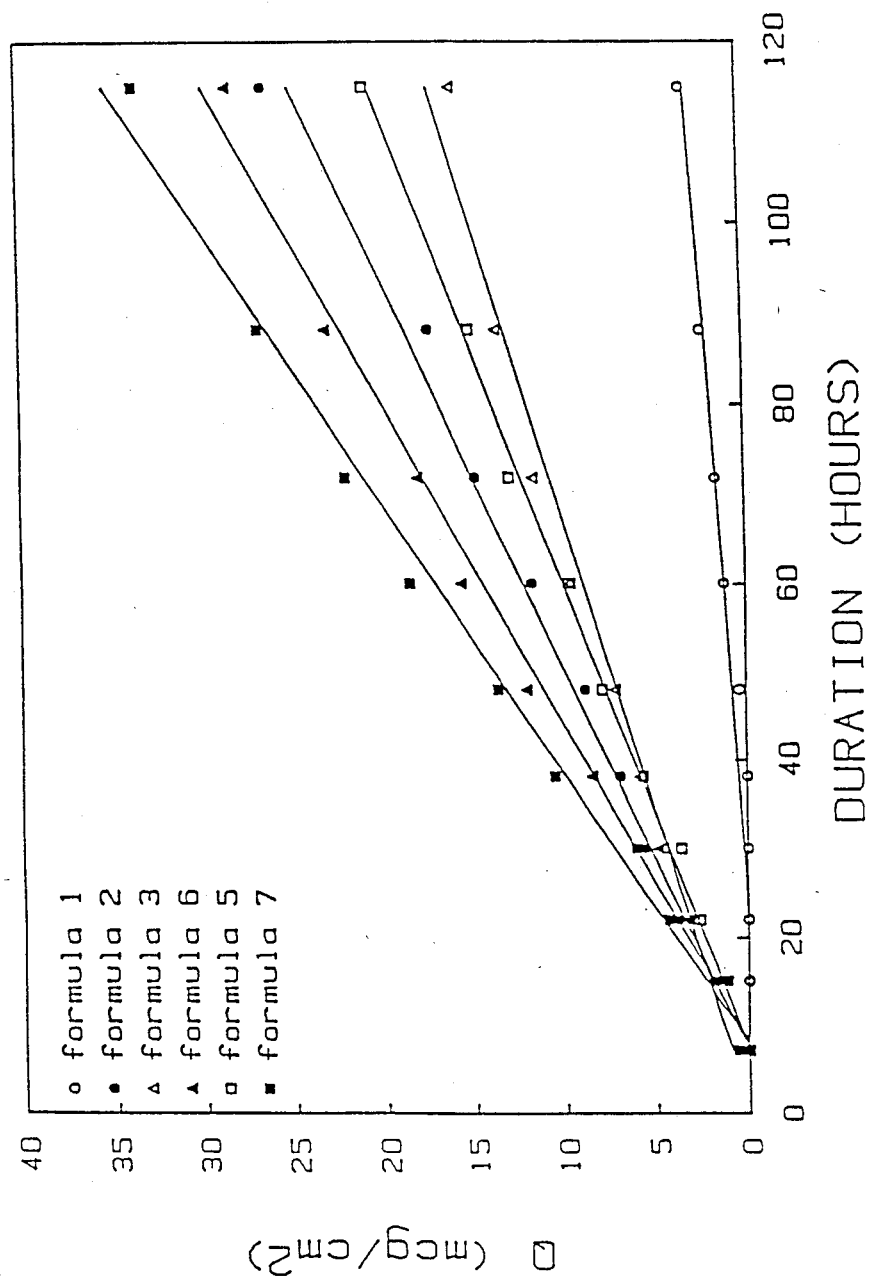
FIG. 1 is a graph of a series of curves showing cumulative (Q) transdermal absorption of ethinyl estradiol from HAD TYPE TDDSH (adhesive type transdermal drug delivery system) through hairless mouse skin using seven different formulas.
Figure 2:
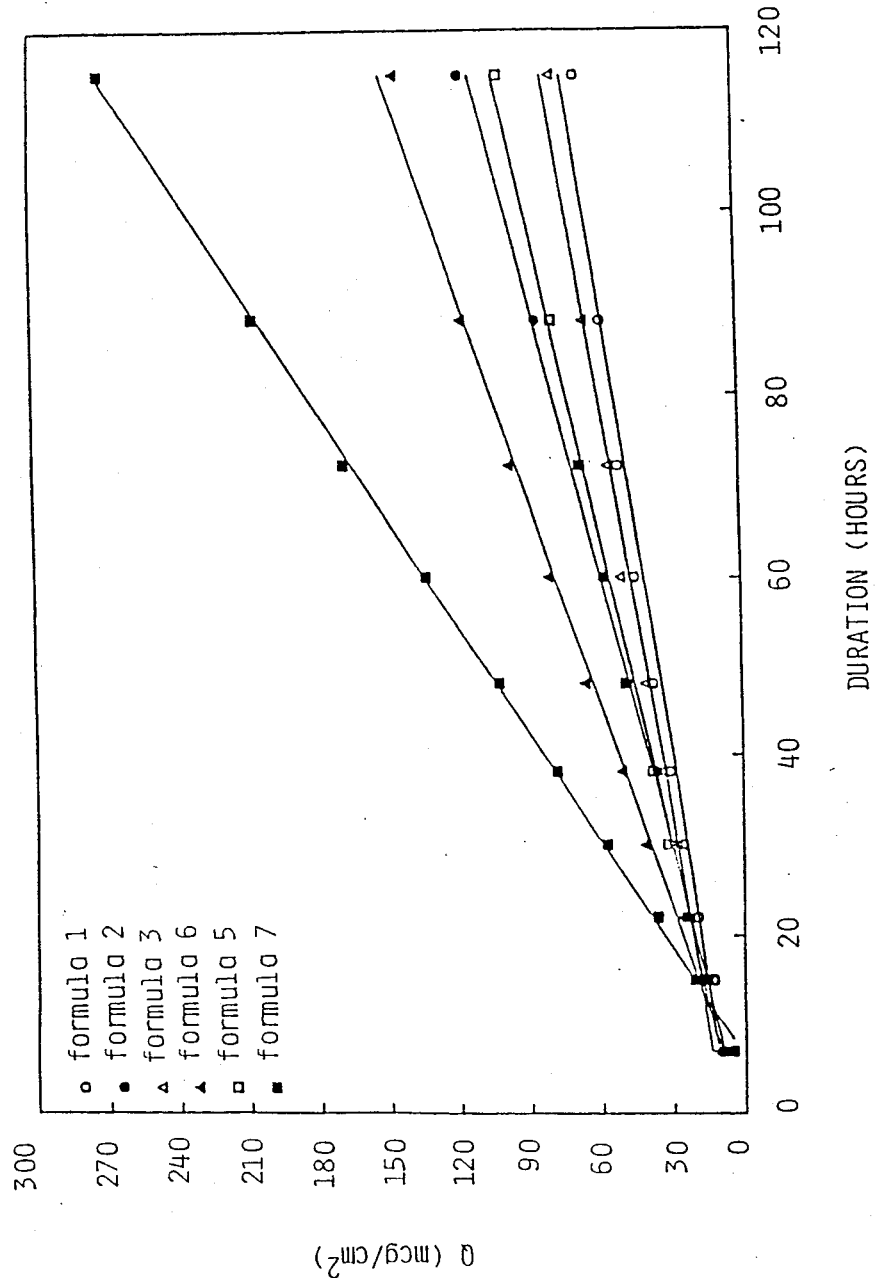
FIG. 2 is a graph of a series of curves showing cumulative (Q) transdermal absorption of norethindrone from adhesive type transdermal drug delivery system through hairless mouse skin using seven different formulas.
Figure 3:
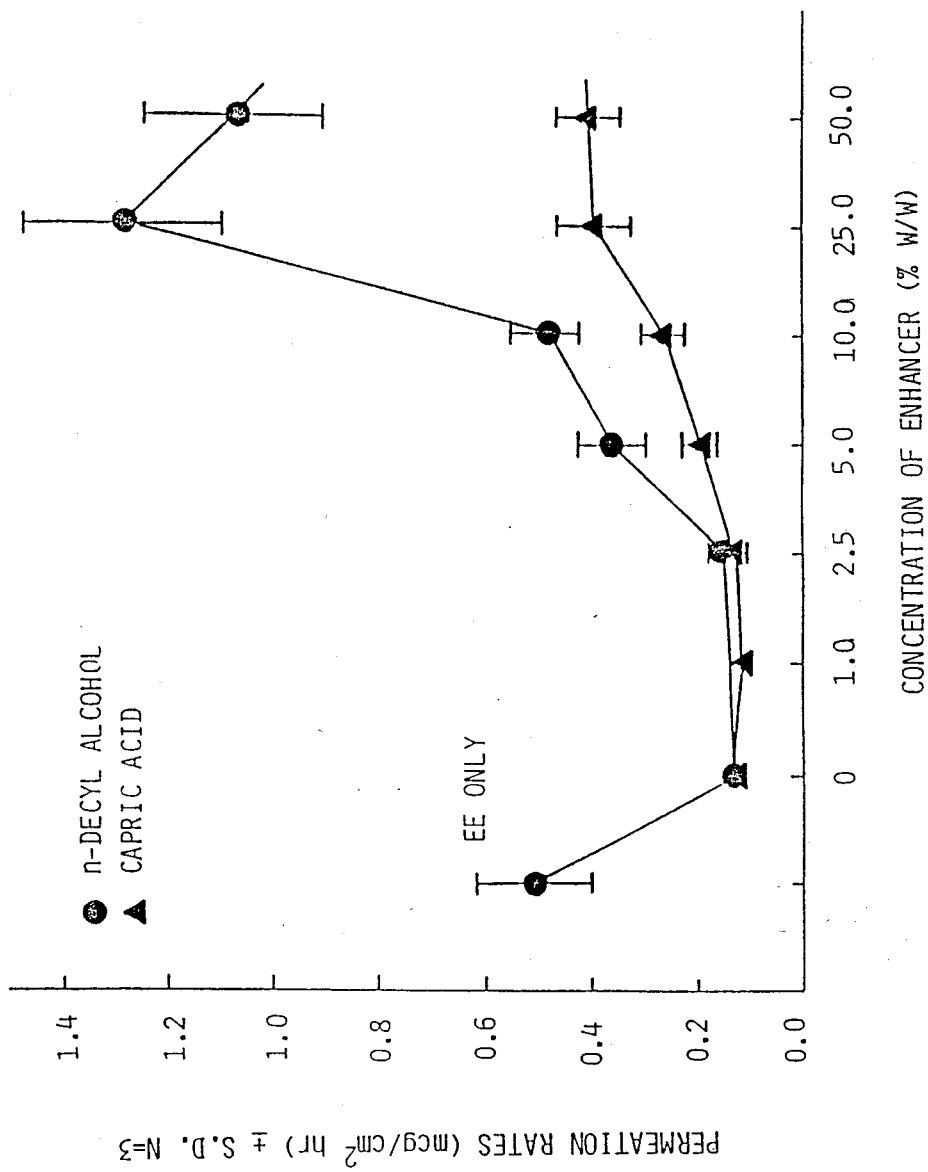
FIG. 3 is a graph showing transdermal absorption rates of ethinyl estradiol across human cadaver skin depending upon transdermal absorption enhancer concentration.
Figure 4:
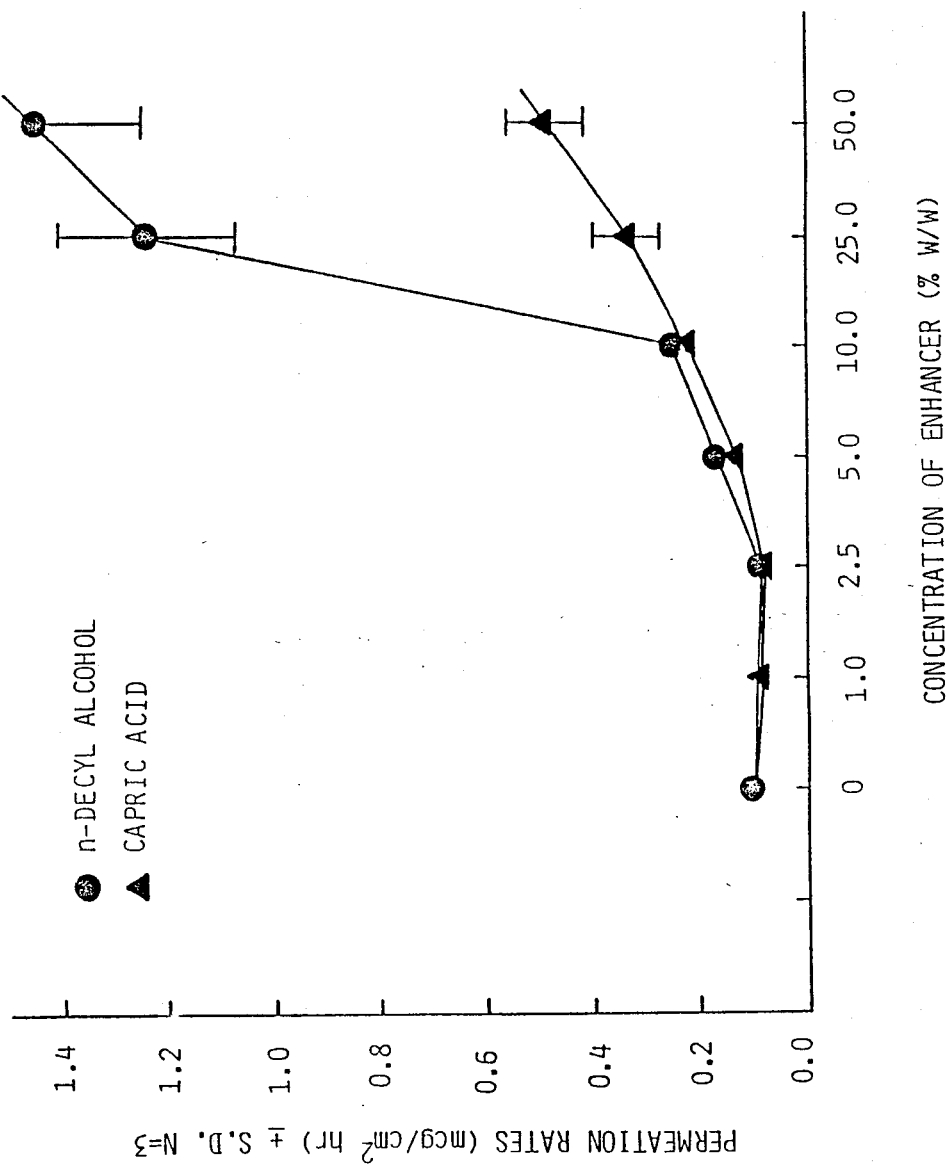
FIG. 4 is a graph showing transdermal absorption rates of norethindrone across human cadaver skin depending upon transdermal absorption enhancer concentration.

The backing layer can be made of any suitable material which is impermeable to the hormones of the polymer layer. The backing layer serves as a protective cover for the polymer layer and provides also a support function. The backing can be formed so that it is essentially the same size layer as the hormone-containing polymer layer or it can be of larger dimension so that it can extend beyond the side of the disc layer or overlay the side or sides of the hormone-containing disc layer and then can extend outwardly in a manner that the surface of the extension of the backing layer can be the base for an adhesive means. For long-term applications, e.g., for seven days, is desirable to use microporous and/or breathable backing laminates, so hydration or maceration of the skin can be minimized. The adhesive means holds the dosage unit in intimate contact with the skin of the subject treated. Examples of materials suitable for making the backing layer are films of high and polyvinylchloride, low density polyethylene, polypropylene, polyurethane, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the polymer layer. The backing layer can be any appropriate thickness which will provide the desired protective and support functions. A suitable thickness will be from about 10 to about 200 microns. Desirably, the thickness will be from about 20 to about 150 microns, and preferably be from about 30 to about 100 microns.

The polymer layer can also be made from polymer adhesives such as polyacrylic, silicone or other suitable polymer adhesives. The polymer layer can also be made, for example, from silicone elastomers of the general polydimethylsiloxane structure, such as silicone polymers of the following general formula:

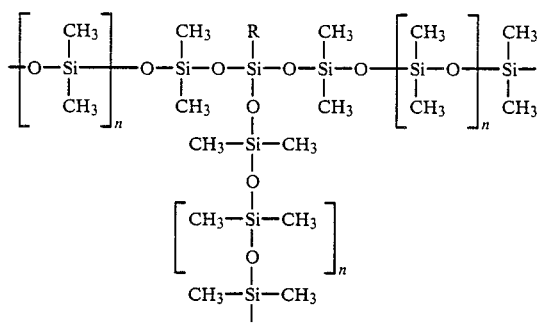

wherein R is alkyl or alkoxy containing 1-7 carbon atoms, vinyl or phenyl and wherein n is about 100 to about 5000.

The silicone polymers selected preferably are cross-linkable at moderate temperatures, such as room temperature, using cross-linking catalysts which are biologically acceptable in the final polymer layer and which are compatible with the hormone components to be used in making the polymer dosage forms. Various suitable crosslinking agents can be used in crosslinking the above polymer, such as tetrapropoxy silane [Si-(OCH$_2$ CH$_2$ CH$_3$)$_4$], if the silicone polymer has free hydroxy groups such as terminal hydroxy groups. A tin catalyst can be used for such crosslinking reaction. If a silicone polymer component has vinyl groups, it can be crosslinked with a dimethyl-silicone polymer using a catalyst such as a platinum catalyst. Some suitable silicone polymers are cross-linkable copolymers having dimethyl and methylvinyl siloxane units, which can be cross-linked as by using a suitable peroxide catalyst. Other cross-linking sites can be present in the polysiloxane elastomers used. Suitable silicone medical-grade polymers are sold under the designations Silastic 382, Q7-4635, Q7-4650, Q7-4665, Q7-4735, Q7-4750, Q7-4765 and MDX-4-4210.

The silicone polymers selected can also have a "block" or "graft" structure or both. By "block" structure is meant that the polymer can have a section or block of the polymer chain structure of the polymer which can have a repeating unit of one type, such as dimethylsiloxane, and then have a succeeding block made up of repeating units of another type, such as methylvinylsiloxane, diphenylsiloxane, diisopropyl siloxane units or other siloxane or silane units or even of monomer units of a compatible non-siloxane or non-silane type. The blocks can vary in length and be repeated as desired. For example, if the blocks are represented as "A" and "B", respectively, the block copolymer can be A-B or A-B-A or A-B-A-B, etc. The "graft" structure simply means that to the main polymer chain, one or more polymer chains are attached. Those grafted chains can have the same polymer units as those of the main chain or can be different, as described above in connection with "block" copolymers. Also, the polymer used can be of a different type wherein copolymerizable monomers are placed together in a polymerization reactor so the main chain can have a certain population of each of the monomeric units.

The following are examples of block copolymers of the type which can be utilized in this invention.

"A" Block

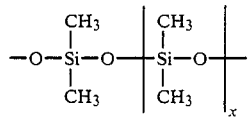

"B" Block

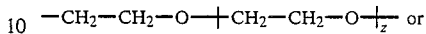

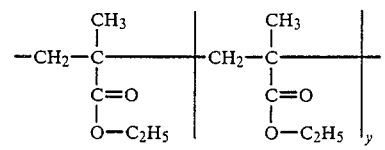

wherein x, y and z represent the number of repeating units sufficient to provide the desired property in the polymer, such as from about 10 to about 5000.

Generally, those polymers used to form biologically acceptable polymer layer are those capable of forming thin walls or coatings through which hormones can pass at a controlled rate. Suitable polymers are biologically and pharmaceutically compatible, non-allergenic and insoluble in and compatible with body fluids or tissues with which the device is contacted. The use of soluble polymers is to be avoided since dissolution or erosion of the matrix would affect the release rate of the hormones as well as the capability of the dosage unit to remain in place for convenience of removal.

Exemplary materials for fabricating the biologically acceptable polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylate, chlorinated polyethylene, polyvinyl chloride, vinyl chloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylene-vinyloxyethanol copolypolymer; silicone copolymers, for example, polysiloxane-polycarbonate copolymers, polysiloxane-polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methyl cellulose, and cellulose esters; polycarbonates; polytetrafluoroethylene; and the like. For best results, the biologically acceptable polymer layer should be selected from polymers with glass transition temperatures below room temperature. The polymer may, but need not necessarily, have a degree of crystallinity at room temperature. Cross-linking monomeric units or sites can be incorporated into such polymers. For example, cross-linking monmers can be incorporated into polyacrylate polymers, which provide sites for cross-linking the polymer layer after microdispersing the hormones into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

The adhesive and polymer layers are suitable made using a silicone adhesive, such as a (polydimethylsiloxane-silicate resin) copolymer adhesive depicted by the following formula:

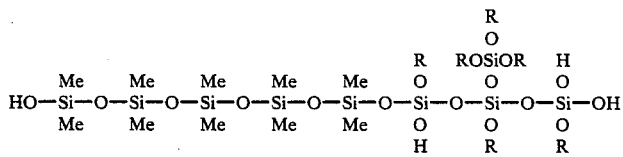

wherein Me is methyl and R is —Si(CH$_3$)$_3$ and x and y represent independent numbers of repeating units sufficient to provide the desired properties in the adhesive polymer and other polymer layers.

For example, adhesive polymer products or amine-resistant adhesive polymer products sold by Dow Corning, such as the ones sold under the designations of DC-355 and X7-2920 medical adhesives, are suitable for use in making the adhesive layer. The adhesive polymer must be biologically acceptable and compatible with the hormones and skin permeation enhancer, if used. Certain polyacrylic adhesive polymers (in the form of an alkyl ester, amide, free acid, or the like) or polyisobutylene adhesive polymers can also be used with some hormones. Illustrative of suitable adhesive polymers for use in making the polymer layer are shown by the following formulas:

Polyisobutylene Adhesive

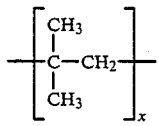

Polyacrylic Adhesive

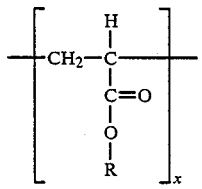

wherein x represents the number of repeating units sufficient to provide the desired properties in the adhesive polymer and R is H or lower alkyl including ethyl, butyl and 2-ethylhexyl.

Other suitable hypoallergenic pressure-sensitive contact adhesive compositions can also be used. A preferred adhesive layer is pressure-sensitive.

However, depending upon pharmaceutical compatibility and other factors, if desired, the adhesive means can be in the form of a ring attached, for example, to an extended portion of the backing layer so that the adhesive layer is adjacent to the sidewall of the hormone-containing disc layer. The width of such adjacent adhesive ring must be adequate to hold the dosage unit securely to the subject being treated. Ordinarily, a suitable width of such adhesive ring can be about 0.2 to about 1.2 cm, preferably about 0.3 to about 1.0 cm.

The adhesive layer then is finally covered with a releasable protective film layer which is made from materials which are substantially impermeable to the hormones, the skin permeation enhancer, if used, and any other components of the dosage unit. The polymer materials and metal foil laminates used for the backing layer may also be used to make the protective layer, provided the layer is made strippable or releasable such as by applying conventional siliconizing or teflon coating. A suitable releasable material for use with silicone polymer adhesive DC-355 and X7-2970 is Scotchpak 1022 material sold by the 3M Company or Bio-Release Material by Dow Corning.

In making the hormone-containing polymer layer, silicone elastomers, such as (polydimethylsiloxane-silicate resin) copolymer, polyacrylic adhesive, such as sold under the designation Duro-Tak, of the formula described above, and other biocompatible adhesive polymers which provide a stable environment for the hormones and permit their release, can suitably be used. In making hormone-dispersed dosage units, it has been found suitable to use a dispersing agent, such as lactose and silica. Other suitable dispersing agents can also be used instead so long as they are effective. Other suitable dispersing agents known to the formulating art can be used. Depending upon the hormones and the drug loading desired, a suitable amount of a dispersing agent can be varied from zero to about 20 percent (by weight) based on the weight of the polymer layer. Commonly, the dispersing agent is added together with the hormone into the polymer used in making the layer. The amount of dispersing agent added is dependent upon the rate of permeation desired, the particular hormones used, and at times, other factors. The amount of the hormones added depends upon the amount of hormone dosage and the duration of treatment desired in each dosage unit and the amount which can be incorporated into the polymer layer to retain suitable structural, diffusion and other properties in the final polymer layer. It has been found, for example, that the hormones can be satisfactorily added to 50 parts of the polymer used in making the polymer layer, such as polyacryic adhesive polymer. It has been found to be preferable to add and disperse the estrogen used in an amount of a selected adhesive polymer. The mixture of the polymer and hormones is then thoroughly mixed using a high-torque mixer to form a homogeneous solution or microdispersion of the hormones in the polymer. After the mixing step, the composition is subjected to vacuum to remove entrapped air.

The deaereated mixture is then applied as by solvent casting technique, to a suitable substrate, like backing laminate or release liner, and heated to a suitable elevated temperature to remove the solvent. The temperature used should not cause significant degradation of the hormones. The polymer sheet desirably is about 10 to 400 microns, preferably about 20 to about 300 microns, in thickness. The resulting medicated polymer sheet is removed from the casting machine and another layer of medicated polymer, containing the same or different hormone, can be further coated on the first medicated polymer layer formed by direct casting or lamination.

The optional separating layer can be made of the adhesive or other materials described for use in making the adhesive layer having progestin present. In making the separating layer, it has been found suitable to use a bio-acceptable polyisobutylene having a suitable molecular weight. For example, the poylisobutylene use can suitably have a relative molecular mass Mv (viscosity average) of from about 800,000 to about 900,000, such as that of polyisobutylene sold by BASF under the designation Oppanol B80, which has a relative molecular mass Mv (viscosity average) value of 850,000. The viscosity average relative molecular mass is obtained from the equation: $J_o = 3.06 \times 10^{-2} \times M\ 0.65$. The viscosity or molecular weight should, generally speaking, be selected which is sufficiently high to provide a separating layer which is dimensionally stable and which is not excessively high so as to make fabrication of the separating layer unnecessarily difficult to provide a functional and pharmaceutically elegant dosage unti.

The thickness of the separating layer can vary as desired. However, it has been found that a layer thickness after any solvent removal of about 50 to about 150 microns to be suitable, with a thickness of about 75 to 125 microns to be preferable. It has been found that a separating layer having about 100 micron thickness made of a polyisobutylene having a viscosity or molecular weight such as that of Oppanol B80 to function well, if the estrogen in the polymer layer is 17-beta-estradiol or ethinyl estradiol.

The separating layer should have sufficient thickness to minimize any migration, especially under prolonged storage conditions at elevated temperatures, such as 37° C. or 45° C. or greater. Also, the separating layer should be made of a suitable material and with a sufficient thickness to decelerate the rate of transmission of the estrogen in the polymer layer, as needed to provide suitably a delivery ratio of transdermal absorption from 10-30/1, a ratio of about 12 to about 20 being a preferable ratio range.

It has been found that the separating layer can be made as by dissolving about 10 parts of a suitable polyisobutylene, such as Oppanol B80 polyisobutylene in a suitable solvent, such a a mixture of cyclohexane, hexane and heptane (for example, a 1:1:1 mixture). The mixture is gently agitated such as by using a suitable rotator.

When the dissolution is substantially complete to provide a clear polyisobutylene solution, the solution can be used to coat a low adhesion film, such as a polyester film with a fluoropolymer-coated surface such as the material sold by 3M Company under the designation Scotch-Pak 1022. A R.D. wireless coating bar (such as a #12) can be used for coating. The resulting coating is dried and is repeated as necessary to obtain a layer of desired thickness, such as 100 microns. The separating layer thus formed can be assembled into the dosage unit by lamination to the polymer layer. Alternatively, the separating layer can be applied to the upper surface of the adhesive layer having present progestin before being assembled by lamination to the lower surface of the polymer layer having present estrogen. The finished multilayered polymer layer can then be cut to form discs with desired shapes and sizes. The polymer layer disc generally should not exceed about 100 sq. cm in area, suitably about 5 to 100 sq. cm, preferably, about 8 to about 80 sq. cm, generally about 10 to 60 sq. cm being more preferable. The shape of the layer discs can vary; they can be circular, square, rectangular or other desired shape.

The hormone-containing polymer layer, generally speaking, may contain some excess of the dispersed hormone over the dosage amount desired to be transdermally absorbed by the subject to be treated. Ordinarily, this excess is small, such as less than 2-fold excess over a weekly projected dose, depending upon the physiochemical properties of the hormones, as well as the nature of the polymer in the polymer layer disc and other factors.

The adhesive means, if it contains a skin permeation enhancer, is made as by dissolving the enhancer and the progestin directly in the adhesive polymer solution or in a solvent which is compatible with the adhesive polymer solution used to make the adhesive layer containing the skin permeation enhancer. Any suitable amount of solvent can be used as necessary to dissolve the quantity of enhancer and progestin to be admixed with the adhesive polymer solution used. For example, 3 to 10 parts of solvent can be used to dissolve one part of skin permeation enhancer, depending upon the solubility of the enhancer. When using polydimethylsiloxane adhesive solution, it has been found suitable to use 2 to 20 parts of skin permeation enhancer in 20 to 50 parts of solvent (such as acetone, methyl ethyl ketone, trifluorotrichloroethane or other suitable solvent) and add the solution to 100 parts of the adhesive solution. The enhancer-adhesive combination is throughly mixed and a coating thereof is applied using a film coating machine, such as referred to in the art as a K-bar coater, directly onto the polymer layer or to a strippable release liner before laminating onto the polymer layer, as described above. A suitable release liner is a poly(ethylene phthalate) laminated with aluminum foil or a Teflon-coated polyester film such as sold under the designation Scotchpak 1022 or Bio-release X7-2741 or X7-2752. The poly(ethylene phthalate) side to which the adhesive-enhancer-progestin coating is applied, is made strippable by conventional siliconizing or by other suitable means. The thickness of the adhesive-enhancer-progestin layer normally is suitable about 20 to about 200 microns, preferably about 30 to about 150 microns.

The amount of enhancer in the adhesive layer depends in part on the rapidity at which it is desired that the hormones be absorbed. Generally speaking, about 1 to about 30 percent of skin permeation enhancer based on the weight of the adhesive is suitable, depending upon the enhancer, adhesive polymer, desired adhesiveness and other factors. Desirably, about 5 to about 20 percent of skin permeation enhancers are used depending upon the above recited factors. The adhesive layer containing the progestin and skin permeation enhancer is transferred to the polymer layer disc surfaces by application of lamination technique under a constant pressure. In order to assure adequate adhesion of the adhesive polymer layer to the skin of the subject treated, additional adhesive polymer coating having a relatively low concentration of enhancer, e.g., 1–5 percent based on the weight of the adhesive polymer can be further applied to the surface of progestin-enhancer-polymer layer. The thickness of this coating ordinarily is a minor percentage of the thickness of the final adhesive layer, such as 20–40 percent of the total adhesive polymer layer. In the progestin-containing adhesive layer having a suitable higher concentration of the enhancer is used. Suitable higher concentrations of enhancer are usually 10 to about 30 percent based on the adhesive polymer weight, the solubility and desired final amount of skin enhancer agent and other factors. The solvent of the respective coatings is removed by evaporation. The respective coatings can be combined to make the final multilayered fertility-control transdermal dosage form by application of lamination technique under a constant pressure or sequential solvent casting technique.

The multi-layer transdermal hormone dosage units are excised. The backing layer, if desired, can be shaped around the sides of the dosage unit, including the polymer layer, if such protection is desired. The resulting hormone polymer dosage unit forms are then placed in appropriate packaging for storage until they are to be applied in transdermal treatment.

At least one estrogen and at least one progestin as defined above are dissolved and/or microdispersed in the polymer and adhesive layers, respectively. With the controlled release of the hormones at a relatively steady rate over a prolonged period, typically several days and preferably one week, the subject is provided with the benefit of a steady infusion of the hormones over a prolonged period.

One of the presently preferred estrogens is 17-beta-estradiol. It is a natural hormone and ordinarily transdermally delivered by an adaptable system of this invention at a desirable daily rate. The 17-beta-estradiol is compatible and can be dissolved or microdispersed in the polymer. The transdermal dosage unit designed for one-week therapy is required to deliver at least about 100 to about 500 mcg (preferably about 125 to about 250 mcg)/day of norgestimate or about 1000 mcg/day of norethindrone and 20-50 mcg/20 $cm^2$/day of 17-beta-estradiol (or an equivalent effective amount of ethinyl estradiol or another estrogen). In fertility control, that amount of progestin is believed to be necessary to inhibit ovulation and that amount of estrogen is believed needed to maintain normal female physiology and characteristics. Derivatives of 17-beta-estradiol which are biocompatible, capable of being absorbed transdermally and preferably bioconvertible to 17-beta-estradiol can also be used, if the amount of absorption meets the required daily dose of the estrogen component and if the hormone components are compatible. Such derivatives of estradiol can be selected from esters, either mono- or di-esters. The mono-esters can be either 3- or 17-esters. The estradiol esters can be, illustratively speaking, estradiol-3,17-diacetate; estradiol-3-acetate; estradiol-17-acetate; estradiol-3,17-divalerate; estradiol-3-valerate; estradiol-17-valerate; 3-mono, 17-mono and 3,17-dipivilate esters; 3-mono, 17-mono and 3,17-dipropionate esters; corresponding cypionate, heptanoate, benzoate and the like esters; ethinyl estradiol; estrone; and other estrogenic steroids and derivatives thereof which are transdermally absorbable, including benzestrol, chlorotrianisene, dienestrol, mestranol, and the like.

The progestin can be and presently preferably is norethindrone or norgestimate or combinations thereof. However, other suitable progestins can be used in place thereof or in combination therewith. For example, a progestin can be selected from levonorgestrel, norethynodrel, dydrogesterone, ethynodiol acetate, hydroxyprogesterone caproate, medroxyprogesterone diacetate, norethindrone acetate, norgestrel, progesterone, and the like.

It will be suggested to those skilled in the art to use other estrogens or progestins in forming the dosage units of this invention. Such use of other estrogens and progestins are intended to be within the scope of this invention insofar as use thereof provides satisfactory dosage units within the spirit of this invention.

The skin permeation enhancers which can be used in carrying out this invention can vary. Ones that give preferred results with the polymer dosage unit form having a specific hormone can vary. In some instances, the use of permeation enhancer in making a dosage unit will result in good or even excellent absorption for one hormone, may result in no or relatively low enhancement when another hormone is used. Use of combinations of two or more of the skin permeation enhancer compounds frequently result in superior results, such as greater transdermal absorption.

Specific skin permeation enhancers which can be used in making the polymer dosage forms of this invention include saturated and unsaturated fatty acids and their esters, alcohols, monoglycerides, acetate, diethanolamides and N, N-dimethylamides, such as oleic acid, propyl oleate, oleyl acetate, propyl myristate, isopropyl myristate, myristyl alcohol, myristyl N, N-dimethyl amide, stearic acid and stearyl alcohol, stearyl propyl ester, monostearin, and combinations of them with, for example, 1-dodecylazacycloheptan-2-one sold under the trademark Azone by Nelson Research and Development; decyl methyl sulfoxide, dimethyl sulfoxide, salicylic acid and derivatives, N,N-diethyl-m-toluamide, crotamiton, 1-substituted azacycloalkan-2-ones such as disclosed in U.S. Pat. No. 4,316,893 (the 1-substituent having 0-17 carbon atoms, preferably, 1-11 carbon atoms), and various other compounds which are biologically compatible and have transdermal permeation enhancement activity. It has been found that n-decyl alcohol is a preferred enhancing agent. Also, it has been found that capric acid is a preferred enhancing agent. Modifications will be suggested to those skilled in the art to the chemical structures represented by n-decyl alcohol or capric acid which do not detract substantially from their function as preferred enhancing agent. It has been found that about 10 to about 40 percent (W/W) of n-decyl alcohol or capric acid is ordinarily a suitable amount. It has been found that about 20 to about 35 percent (W/W) in the adhesive layer of these enhancing agents provide highly satisfactory skin absorption enhancement and satisfactory adhesion. Amounts higher than 35 or 40 percent (W/W) can diminish skin absorption enhancement and interfere with satisfactory adhesion to the subject being treated.

Ethyl alcohol and other short chain alkanols (with 1-4 carbon atoms) which have substantially the same properties and activity as ethyl alcohol do not come within the definition of skin permeation enhancer as used herein.

The following examples are in illustration of the invention and are not intended to be limiting.

EXAMPLE 1

The following ingredients are used in making the estrogen-containing polymer layer: ethinyl estradiol, 5 parts; polyacrylic adhesive sold by National Starch and Chemical Corp. as Duro-Tak 80-1054, 100 parts.

The ethinyl estradiol is added to the polyacrylic adhesive using a high torque mixer (sold by Cole-Parmer Company) at a rate of about 1000 RPM.

The hormone mixture is applied to the backing layer formed of polyester/aluminum laminate sold by 3M Company as Scotch-Pak 1005, by using a K-bar coater equipped with a number 3 bar. The resulting polymer layer is dried in the hood for one hour to remove the solvents. The thickness of the polymer layer obtained is about 10 microns.

To the polymer layer, a 5% (W/W) norethindrone in polyacrylic adhesive solution is applied using a K-bar coater (with #16 bar). In addition to norethindrone, this coating solution also contains 25% (W/W) of n-decyl alcohol as skin permeation enhancer. The coating is dried at ambient room temperature for 24 hours. The dried norethindrone-reservoir adhesive layer has a dry thickness of about 120 microns.

The bilayer dosage units are then covered with a transparent low-adhesion release liner (Scotch-Pak 1022/3M). The completed dosage layers are then cut into dosage units having various shapes and sizes by using a specially-designed device cutter, such as a 20 cm² rectangular shape.

The transdermal absorption of the hormones from the anti-fertility polymer dosage units of this invention is evaluated by using a skin specimen from a "hairless" mouse or human cadaver by following the procedure described by Y. W. Chien, K. Valia and U. B. Doshi in *Drug Develop. & Ind. Pharm.*, 11(7) 1195–1212 (1985).

Transdermal polymer dosage units are obtained following generally the procedures described above and evaluated as shown in the following Tables 1–3.

TABLE 1

Rates of Permeation[1] for Ethinyl Estradiol and Norethindrone Across Hairless Mouse Skin[2]

| Formulation | Enhancer | Permeation Rate (mcg/cm²/hr ± S.D.) Ethinyl Estradiol[3] | (n = 3) Norethindrone[4] |
|---|---|---|---|
| 1 | none | 0.04 (± 0.01) | 0.45 (± 0.07) |
| 2 | IPM | 0.25 (± 0.05) | 0.97 (± 0.19) |
| 3 | DMSO | 0.13 (± 0.02) | 0.52 (± 0.14) |
| 4 | DeMS | 0.16 (± 0.03) | 0.39 (± 0.07) |
| 5 | LA | 0.19 (± 0.03) | 0.76 (± 0.20) |
| 6 | OA | 0.26 (± 0.04) | 1.21 (± 0.22) |
| 7 | DeA | 0.30 (± 0.06) | 2.51 (± 0.49) |
| 8 | CA | 0.25 (± 0.04) | 2.04 (± 0.30) |

[1] 12 samples were taken during 115 hours of study.
[2] Seven-week-old female hairless mouse abdominal skin.
[3] Loading dose: 30.5 (± 1.3) mcg/cm²
[4] Loading dose: 338.0 (± 10.1) mcg/cm²
IPM (isopropyl myristate); DMSO (dimethyl sulfoxide); DeMS (decyl methyl sulfoxide); LA (lauric acid); OA (oleic acid);

TABLE 2

Rates of Permeation[1] for Ethinyl Estradiol and Northindrone Across Human Cadaver Skin[2]

| Formulation | Enhancer | Permeation Rate (mcg/cm²/hr ± S.D.) Ethinyl Estradiol[3] | (n = 3) Norethindore[4] |
|---|---|---|---|
| 1 | none | 0.02 (± 0.004) | 0.14 (± 0.03) |
| 2 | IPM | 0.09 (± 0.02) | 0.39 (± 0.07) |
| 3 | DMSO | 0.04 (± 0.01) | 0.17 (± 0.03) |
| 4 | DeMS | 0.05 (± 0.01) | 0.12 (± 0.02) |
| 5 | LA | 0.07 (± 0.02) | 0.26 (± 0.04) |
| 6 | OA | 0.09 (± 0.02) | 0.46 (± 0.09) |
| 7 | DeA | 0.13 (± 0.02) | 0.89 (± 0.18) |
| 8 | CA | 0.07 (± 0.01) | 0.80 (± 0.14) |

[1] 12 samples were taken during 122 hours of study.
[2] A 17-year-old black boy's left anterial leg with average thickness of 220 (± 26) microns.
[3] Loading dose: 30.5 (±1.3) mcg/cm².
[4] Loading dose: 338.0 (± 10.1) mcg/cm².

TABLE 3

Enhancing Effect of Skin Permeation Enhancer on the Skin Permeation Rates[1] of Ethinyl Estradiol and Norethindrone Across Human Cadaver Skin[2]

| Formulation | Enhancer | Permeation Rate (mcg/cm²/hr ± S.D.) Ethinyl Estradiol[3] | (n = 3) Norethindrone[4] |
|---|---|---|---|
| n-Decyl Alcohol (% w/w) | | | |
| 9 | 0 | 0.13 (± 0.02) | 0.10 (± 0.02) |
| 10 | 2.5 | 0.15 (± 0.03) | 0.09 (± 0.02) |
| 11 | 5.0 | 0.36 (± 0.06) | 0.17 (± 0.03) |
| 12 | 10.0 | 0.48 (± 0.07) | 0.25 (± 0.04) |
| 13 | 25.0 | 1.28 (± 0.19) | 1.24 (± 0.18) |
| 14 | 50.0 | 1.06 (± 0.18) | 1.45 (± 0.21) |
| Capric acid (% w/w) | | | |
| 15 | 1.0 | 0.12 (± 0.02) | 0.08 (± 0.01) |
| 16 | 2.5 | 0.13 (± 0.02) | 0.08 (± 0.01) |
| 17 | 5.0 | 0.19 (± 0.03) | 0.13 (± 0.02) |
| 18 | 10.0 | 0.26 (± 0.04) | 0.23 (± 0.04) |
| 19 | 25.0 | 0.39 (± 0.07) | 0.33 (± 0.05) |
| 20 | 50.0 | 0.40 (± 0.06) | 0.49 (± 0.10) |

[1] 13 samples were taken during 168 hours of study period.
[2] A white male's anterial trunk with average thickness of 180 ± 20 microns (n = 6) were used.
[3] Loading dose: 95.7 (± 2.9) mcg/cm²
[4] Loading dose: 1.26 (± 0.03) mg/cm²

EXAMPLE 2

The formulations of the above Tables are repeated using the following procedure.

The following ingredients are used in making the estrogen-containing polymer layer: ethinyl estradiol, 5 parts; polyacrylic adhesive sold by National Starch and Chemical Corp. as Duro-Tak 80-1054, 100 parts.

The ethinyl estradiol is added to the polyacrylic adhesive using a high torque mixer (sold by Cole-Parker Company) at a rate of about 1000 RPM.

The hormone mixture is applied to the backing layer formed of polyester/aluminum laminate sold by 3M Company as Scotch-Pak 1005, by using a K-bar counter equipped with a number 3 bar. The resulting polymer layer is dried in the hood for one hour to remove the solvents. The thickness of the polymer layer obtained is about 10 microns.

To the polymer layer, a 5% (W/W) norethindrone in polyacrylic adhesive solution is applied on a transparent low-adhesion substrate using a K-bar coater (with #16 bar). In addition to norethindrone, this coating solution also contains 25% (W/W) of n-decyl alcohol as skin permeation enhancer. The coating is dried in the hood at ambient room temperature for 24 hours. The dried norethindrone-reservoir adhesive layer has a thickness of about 120 microns.

The norethindrone layer is carefully applied to the ethinyl estradiol layer by lamination technique. The completed dosage layers are then cut into dosage units having various shapes and sizes by using a specially-designed device cutter, such as 20 cm² rectangular shape.

EXAMPLE 3

Figure 5:
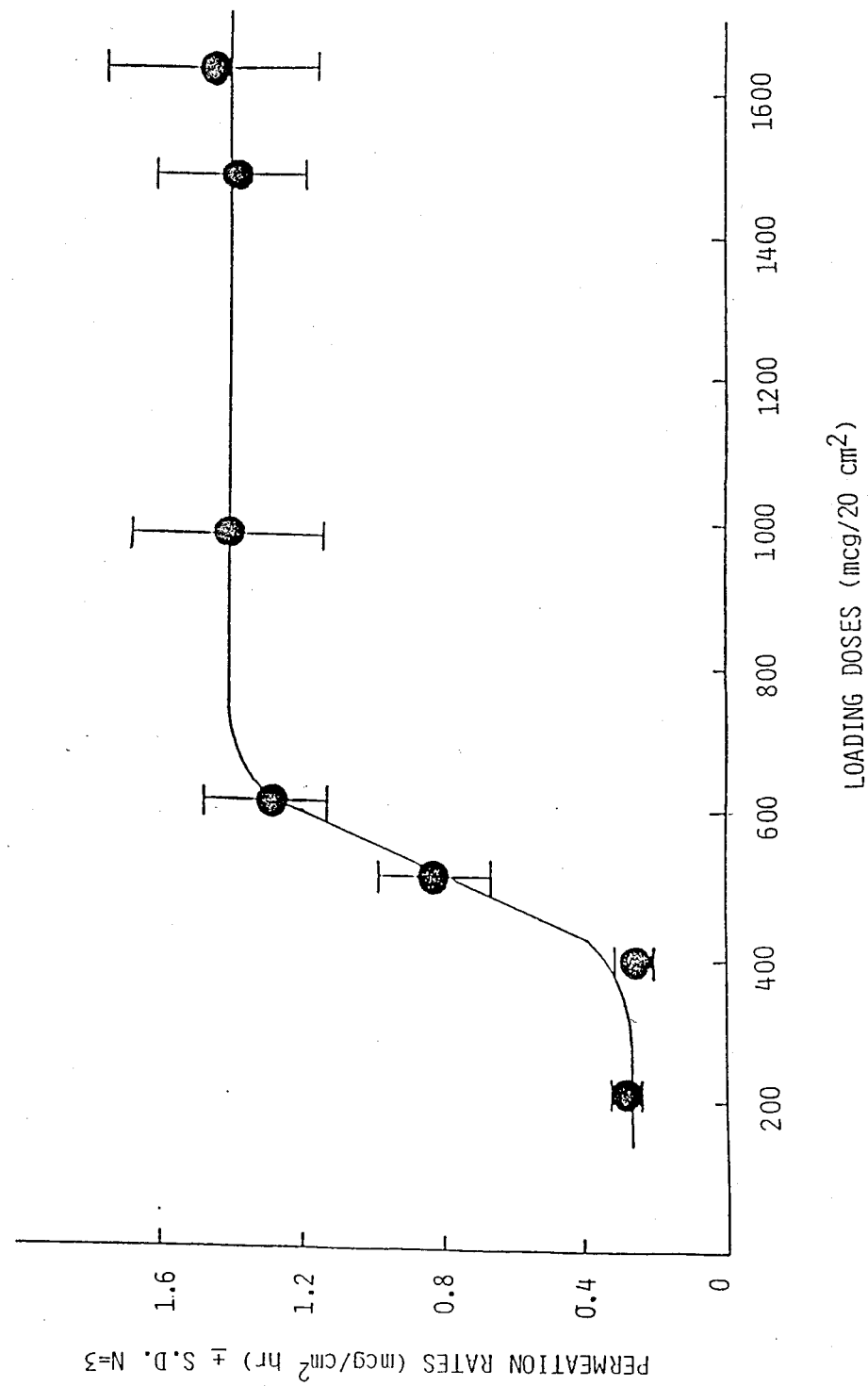
FIG. 5 is a graph showing transdermal absorption ratio of ethinyl estradiol through human cadaver skin from dosage units of the invention in which both the polymer layer and adhesive layer are made from adhesive polymer.

Example 1 is repeated except the ethinyl estradiol loading in the polymer layer is varied from 200 mcg/20 cm² to 1600 mcg/20 cm². The above formulation 13 is used. The data show that the rate of permeation across human skin increases as the loading of ethinyl estradiol increases until the loading concentration reaches about 1600 mcg/20 cm², at which point increased loadings according to the data of the experiment do not provide increased permeability. This is shown in the chart of FIG. 5.

EXAMPLE 4

Examples 1 and 2 are repeated except bioactively equivalent amounts of 17-beta-estradiol are used instead of ethinyl estradiol.

EXAMPLE 5

Examples 1 and 2 are repeated except bioactively equivalent amounts of norgestimate are used instead of norethindrone.

EXAMPLE 6

Examples 1 and 2 are repeated except bioactively equivalent amounts of 17-beta-estradiol and norgestimate are used instead of ethinyl estradiol and norethindrone, respectively.

EXAMPLE 7

Examples 1, 2, 4, 5 and 6 are repeated using polydimethylsiloxane adhesive instead of the polyacrylic adhesive.

EXAMPLE 8

The following ingredients are used in making a trilayer transdermal estrogen/progestin dosage unit:

(I) Ethinyl estradiol, 1 part; polyacrylic adhesive (sold by National Starch and Chemical Corp., as Duro-Tak 80-1054), 99 parts. The ethinyl estradiol is dissolved in the polyacrylic adhesive by gently rotating the container using rotator (Cole-Parmer Company) at low speed (10 rpm) to form a clear solution. This hormone/adhesive mixture is applied by coating to a sheet of polyester/aluminum laminate (sold by 3M Company as Scotch-Pak 1109), on the polyester surface, using a R.D. wireless-coating bar (#8). The resulting polymer layer is dried in the hood for one hour to remove the solvent portion. The thickness of the dried estrogen reservoir polymer adhesive layer obtained is about 40 microns.

(II) Polyisobutylene polymer (sold by BASF, as Oppanol B80), 10 parts; 1:1:1 mixture of cyclohexane/hexane/heptane as solvent system for Oppanol B80, 90 parts. The polyisobutylene polymer is dissolved in the solvent system in a closed container by gently rotating the container using a rotator (Cole-Palmer Company) at low speed (10 rpm) until all the polymer is dissolved and a clear solution is formed. This polymer solution is applied to the low-adhesion side of a substrate (a polyester film with fluoropolymer-coated surface, sold by 3M Company as Scotch-Pak 1022) using R.D. wireless coating bar (#12). This polymer coating is dried in the hood for 2 hours. The resulting dried polymer film has a thickness of about 100 microns.

(III) Norethindrone, 5 parts; n-decyl alcohol, 35 parts; polyacrylic adhesive (sold by National Starch and Chemical Corp. as Duro-Tak 80-1054), 60 parts. The norethindrone is dispersed in n-decyl alcohol by rotating gently the container using a rotator (Cole-Palmer Company) at low speed (10 rpm) to form a drug suspension. The polyacrylic adhesive is then added to the suspension and the mixture is rotated gently again using the same rotator at a speed of 10 rpm until a homogeneous mixture is obtained. The mixture is applied to the low-adhesion side of a substrate (a polyester with fluoropolymer-coated surface, sold by 3M Company as Scotch-Pak 1022) using a R.D. wireless coating bar (#28). This coating layer is dried in the hood for 24 hours. The thickness of the dried norethindrone/n-decyl alcohol reservoir layer obtained is about 250 microns.

The polyisobutylene product of (II) is laminated onto the product of (I) containing ethinyl estradiol. The layer of (III) containing norethindrone is then laminated into the combined laminates (I) and (II), on the surface of layer (II), to form the final product. The final laminated product is cut into specific size using steel die cutter to form the tri-layer transdermal estrogen/progestin dosage unit.

Units of 10 sq cm are individually packed in the paper/foil/polyester pouches which are then thermally sealed by a thermal sealer. These sealed pouches are stored in the stability testing cabinets (Gravity Convection Incubator, sold by GCA Corp.) at three different temperatures, room temperature, 37° C. and 45° C. for up to 26 weeks. During the storage, pouches are randomly sampled at specific intervals, according to the sampling schedule shown in Table 4. The units sealed in the pouches are evaluated for their drug content and skin permeation rate profiles. Drug content in each unit was determined by a solvent extraction procedure followed by a high performance liquid chromatograph (HPLC) of the drugs. The skin permeation rate profiles of drugs released from the unit were determined by a hydrodynamically well-calibrated in-vitro skin permeation cell system. The skin specimen freshly excised from 5-to-7 week old female hairless mouse skin was used as the model skin. The skin permeation study was performed at 37° C. using 40% V/V PEG 400 saline solution as receptor solution. The steady-state skin permeation rate of norethindrone and ethinyl estradiol was determined from the slope of a Q vs time plot, where Q is the cumulative amount of drug permeating through the skin at a specific sampling time interval. It was calculated by determining the drug concentration in the receptor solution by the HPLC assay.

Drug content or skin permeation rate of drug determined from the stability samples were plotted, according to storage temperature, against the storage time. A 95% confidence limit, based on the mean value obtained from the week 0 samples, is established to make statistical judgment on the physical and chemical stability of the unit tested. Data point that falls outside the 95% confidence limit lines is considered as either chemically (from drug recovery study) or physically (from skin permeation study) unstable.

TABLE 4

| Temperature (° C.) | Sampling Schedule (Weeks) | | | | | | |
|---|---|---|---|---|---|---|---|
| | 0 | 1 | 2 | 4 | 8 | 12 | 26 |
| Room | X | — | — | X | X | X | X |
| 37 | X | — | X | X | X | X | X |
| 45 | X | X | X | X | X | X | X |

TABLE 5
Drug Recovery Data of Stability Samples of Dosage Units of Example 8

| Temperature | Sampling Time (Weeks After Storage) | | | | | | |
|---|---|---|---|---|---|---|---|
| | 0 | 1 | 2 | 4 | 8 | 12 | 26 |
| Ethinyl Estradiol (mcg/10 cm² ± S.D.)[1,2] | | | | | | | |
| Room Temp. | 529.7 (32.98) | — | — | 514.5 (35.57) | 527.7 (34.99) | 517.6 (27.89) | 511.1 (31.31) |
| 37° C.) | 552.2 (33.89) | — | 576.8 (37.22) | 539.5 36.67) | 531.1 (29.45) | 538.9 (43.41) | 522.1 (29.82) |
| 45° C. | 540.4 (33.71) | 530.7 (39.98) | 522.7 (37.11) | 539.6 (29.67) | 513.6 (29.98) | 505.7 (42.11) | 495.2 (34.72) |
| Norethindrone (mcg/10 cm² ± S.D.)[1,2] | | | | | | | |
| Room Temp. | 14.18 (0.98) | — | — | 13.43 (1.06) | 13.11 (1.18) | 14.14 (1.32) | 13.01 (1.24) |
| 37° C. | 16.67 (1.09) | — | 15.57 (1.41) | 15.11 (1.11) | 14.40 (1.61) | 14.11 (1.24) | 13.79 (1.18) |
| 45° C. | 15.22 (1.43) | 15.01 (1.14) | 14.77 (1.02) | 14.78 (1.31) | 13.49 (1.29) | 13.29 (1.08) | 13.77 (1.19) |

[1] Mean ± Standard Deviation (N = 3)
[2] Triplicate sample dosage units solvent extracted at indicated storage times and temperatures and the ethinyl estradiol and norethindrone contents determined using high performance liquid chromatography (HPLC).

TABLE 6
Skin Permeation Rate of Stability Samples of Dosage Units of Example 8

| Temperature | Sampling Time (Weeks After Storage) | | | | | | |
|---|---|---|---|---|---|---|---|
| | 0 | 1 | 2 | 4 | 8 | 12 | 26 |
| Ethinyl Estradiol (mcg/10 cm² hr ± S.D.)[1,2] | | | | | | | |
| Room Temp. | 0.20 (0.034) | — | — | 0.26 (0.033) | 0.19 (0.021) | 0.26 (0.033) | 0.22 (0.021) |
| 37° C. | 0.25 (0.027) | — | 0.27 (0.040) | 0.22 (0.018) | 0.29 (0.027) | 0.30 (0.041) | 0.22 (0.031) |
| 45° C. | 0.28 (0.041) | 0.25 (0.022) | 0.21 (0.026) | 0.31 (0.039) | 0.22 (0.033) | 0.23 (0.042) | 0.20 (0.031) |
| Norethindrone (mcg/10 cm² ± S.D.)[1,2] | | | | | | | |
| Room Temp. | 2.46 (0.26) | — | — | 2.38 (0.31) | 2.09 (0.19) | 2.15 (0.25) | 2.57 (0.35) |
| 37° C. | 2.33 (0.31) | — | 2.46 (0.41) | 2.37 (0.35) | 2.72 (0.41) | 2.44 (0.39) | 2.21 (0.34) |
| 45° C. | 2.29 (0.33) | 2.56 (0.37) | 2.33 (0.28) | 2.71 (0.37) | 2.53 (0.37) | 2.56 (0.35) | 2.28 (0.31) |

[1] Mean ± Standard Deviation (N = 3)
[2] Permeation rates of triplicate sample dosage units determined using 5–7 week old female hairless mouse skin in Chien et al. procedure for 146 hours and the rates determined from slope of Q vs permeation time plots.

TABLE 7
Effect of Thickness of Polyisobutylene Layer (Oppanol B80) on Permeation Rates Across Human Cadaver Skin

| Formulation Number | Human Cadaver Skin Permeation Rates[a,b,c,d] (mcg/sq cm hr ± S.D.) | |
|---|---|---|
| | Ethinyl Estradiol | Norethindrone |
| 2-0 | 0.22 (0.041) | 1.15 (0.100) |
| 2-1 | 0.24 (0.033) | 1.03 (0.170) |
| 2-2 | 0.20 (0.021) | 1.24 (0.210) |
| 2-3 | 0.16 (0.029) | 0.97 (0.160) |
| 2-4 | 0.16 (0.031) | 1.19 (0.240) |
| 2-5 | 0.14 (0.021) | 1.04 (0.250) |
| 2-6 | 0.09 (0.017) | 1.26 (0.280) |
| 2-7 | 0.06 (0.014) | 1.06 (0.190) |
| 2-8 | 0.04 (0.010) | 1.17 (0.200) |
| 2-9 | 0.02 (0.006) | 1.06 (0.230) |

[a] 11 samples were taken for each of the triplicate experiments (n = 3) during 146 hours of study.
[b] 40% PEG 400/saline was used as receptor solution.
[c] Anterior trunk of a young caucasian female cadaver skin was used.
[d] Procedure of Chien et al. used, samples taken at times 0, 2, 4, 8, 12, 24, 48, 72, 96, 120, and 146, and rates determined from slopes of Q vs permeation time plots.

TABLE 8
Variation of Permeation Rates of Norethindrone Depending on Content of Enhancer

| Formulation Number | % (W/W) of n-Decyl Alcohol | Norethindrone Skin Permeation Rate[1,2] (mcg/sq cm hr ± S.D.) |
|---|---|---|
| 2-10 | 0 | 0.13 (± 0.02) |
| 2-11 | 10 | 0.31 (± 0.07) |
| 2-12 | 20 | 0.49 (± 0.06) |
| 2-13 | 30 | 0.87 (± 0.17) |
| 2-7 | 35 | 1.10 (± 0.24) |
| 2-14 | 40 | 1.17 (± 0.21) |
| 2-15 | 45 | 1.23 (± 0.29) |

[1] 11 samples were taken for each of triplicate experiments (n = 3) during 146 hours of study.
[2] Procedure of Chien et al. used, samples taken at times 0, 2, 4, 8, 12, 24, 48, 72, 96, 120, and 146, and rates determined from slopes of Q vs permeation time plots.

TABLE 9
Variation of Permeation Rate Ratios Depending on Enhancer Contents

| Formulation Number | % (W/W) of n-Decyl Alcohol | Ratio of Permeation Rates Norethindrone/Ethinyl Estradiol |
|---|---|---|
| 2-10 | 0 | 4.19 (± 0.41) |
| 2-11 | 10 | 8.38 (± 0.77) |
| 2-12 | 20 | 12.56 (± 1.49) |

TABLE 9-continued
Variation of Permeation Rate Ratios Depending on Enhancer Contents

| Formulation Number | % (W/W) of n-Decyl Alcohol | Ratio of Permeation Rates Norethindrone/Ethinyl Estradiol |
|---|---|---|
| 2-13 | 30 | 18.13 (± 2.33) |
| 2-7 | 35 | 18.33 (± 2.74) |
| 2-14 | 40 | 15.39 (± 1.96) |
| 2-15 | 45 | 13.98 (± 1.87) |

TABLE 10
Variation of Permeation Rates of Norethindrone Depending on Content of Enhancer

| Formulation Number | % (W/W) of Capric Acid | Norethindrone Skin Permeation Rate[1,2] (mcg/sq cm hr ± S.D.) |
|---|---|---|
| 2-10 | 0 | 0.13 (± 0.02) |
| 2-16 | 10 | 0.41 (± 0.07) |
| 2-17 | 20 | 0.66 (± 0.11) |
| 2-18 | 30 | 1.16 (± 0.19) |
| 2-19 | 35 | 1.48 (± 0.24) |
| 2-20 | 40 | 1.59 (± 0.34) |
| 2-21 | 45 | 1.84 (± 0.15) |

[1]11 samples were taken for each of triplicate experiments. (n = 3) during 146 hours of study.
[2]Procedure of Chien et al. used, samples taken at times 0, 2, 4, 8, 12, 24, 48, 72, 96, 120 and 146, and rates determined from slopes of Q vs permeation time plots.

TABLE 11
Variation of Permeation Ratios Depending on Enhancer Contents

| Formulation Number | % (W/W) of Capric Acid | Ratio of Permeation Rates Norethindrone/Ethinyl Estradiol |
|---|---|---|
| 2-10 | 0 | 4.19 (± 0.41) |
| 2-16 | 10 | 12.42 (± 1.96) |
| 2-17 | 20 | 14.04 (± 2.11) |
| 2-18 | 30 | 15.68 (± 1.91) |
| 2-19 | 35 | 15.91 (± 1.77) |
| 2-20 | 40 | 12.82 (± 2.01) |
| 2-21 | 45 | 12.35 (± 1.44) |

TABLE 12
Variation of Permeation Rates of Ethinyl Estradiol Depending on Thickness of Adhesive Layer

| Formulation Number | Thickness of Adhesive Layer (Microns) | Ethinyl Estradiol Skin Permeation Rate[1,2] (mcg/sq cm hr ± S.D.) |
|---|---|---|
| 2-22 | 142.8 | 0.079 (± 0.009) |
| 2-23 | 178.5 | 0.070 (± 0.010) |
| 2-24 | 214.2 | 0.066 (± 0.008) |
| 2-7 | 250.0 | 0.060 (± 0.011) |
| 2-25 | 285.6 | 0.066 (± 0.015) |
| 2-26 | 321.7 | 0.074 (± 0.011) |

[1]11 samples were taken for each of triplicate experiments (n = 3) during 146 hours of study.
[2]Procedure of Chien et al. used, samples taken at times 0, 2, 4, 8, 12, 24, 48, 72, 96, 120 and 146, and rates determined from slopes of Q vs permeation time plots.

TABLE 13
Variation of Ratios of Permeation Rates Depending on Thickness of Adhesive Layer

| Formulation Number | Thickness of Adhesive Layer (Microns) | Ratio of Permeation Rates Norethindrone/Ethinyl Estradiol |
|---|---|---|
| 2-22 | 142.8 | 3.92 (± 0.52) |
| 2-23 | 178.5 | 8.00 (± 1.33) |
| 2-24 | 214.2 | 12.27 (± 2.02) |
| 2-7 | 250.0 | 18.33 (± 2.34) |
| 2-25 | 285.6 | 18.03 (± 2.17) |
| 2-26 | 321.7 | 17.16 (± 1.99) |

The following Tables 14 and 15 show data for dosage units without separating layers in comparison with data shown in Tables 5 and 6 for dosage units with separating layers.

TABLE 14
Drug Recovery Data from Stability Samples of Bi-Layer Patch System[2]

| Temperature | Sampling Time (Weeks After Storage) | | | | | | |
|---|---|---|---|---|---|---|---|
| | 0 | 1 | 2 | 4 | 8 | 12 | 26 |
| Ethinyl Estradiol (mcg/10 cm² ± S.D.)[1] | | | | | | | |
| Room Temp. | 566.9 | — | — | 569.4 | 536.8 | 552.2 | 539.9 |
| | (33.18) | | | (34.44) | (33.90) | (33.11) | (35.56) |
| 37° C. | 572.5 | — | 570.0 | 545.1 | 557.5 | 539.9 | 533.6 |
| | (40.26) | | (34.67) | (41.11) | (31.22) | (33.31) | (29.98) |
| 45° C. | 559.4 | 566.9 | 530.5 | 527.7 | 510.0 | 519.8 | 507.6 |
| | (38.88) | (44.76) | (39.77) | (41.12) | (44.17) | (36.66) | (38.98) |
| Norethindrone (mcg/10 cm² ± S.D.)[1] | | | | | | | |
| Room Temp. | 15.52 | — | — | 14.98 | 14.16 | 15.78 | 16.12 |
| | (0.99) | | | (0.92) | (0.79) | (1.05) | (1.11) |
| 37° C. | 16.11 | — | 16.64 | 15.52 | 14.22 | 15.78 | 14.02 |
| | (1.19) | | (0.84) | (0.91) | (0.77) | (1.17) | (0.69) |
| 45° C. | 17.72 | 17.01 | 15.24 | 14.96 | 14.66 | 15.28 | 14.06 |
| | (1.27) | (1.00) | (0.92) | (1.33) | (1.07) | (1.26) | (0.93) |

[1]Mean ± Standard Deviation (N = 3).
[2]Triplicate sample dosage units solvent extracted at indicated storage times and temperatures and the ethinyl estradiol and norethindrone contents determined using high performance liquid chromatography (HPLC).

TABLE 15
Skin Permeation Rate from Stability Samples of Bi-Layer Patch System[2]

| Temperature | \multicolumn{7}{c}{Sampling Time (Weeks After Storage)} |
|---|---|---|---|---|---|---|---|
|  | 0 | 1 | 2 | 4 | 8 | 12 | 26 |
| \multicolumn{8}{c}{Ethinyl Estradiol (mcg/10 $cm^2$ hr ± S.D.)[1]} |
| Room Temp. | 0.59 | — | — | 0.52 | 0.55 | 0.59 | 0.64 |
|  | (0.04) |  |  | (0.06) | (0.05) | (0.04) | (0.08) |
| 37° C. | 0.61 | — | 0.63 | 0.70 | 0.73 | 0.66 | 0.79 |
|  | (0.08) |  | (0.09) | (0.07) | (0.11) | (0.10) | (0.14) |
| 45° C. | 0.66 | 0.69 | 0.76 | 0.77 | 0.74 | 0.77 | 0.87 |
|  | (0.11) | (0.13) | (0.13) | (0.08) | (0.09) | (0.16) | (0.12) |
| \multicolumn{8}{c}{Norethindrone (mcg/10 $cm^2$ hr ± S.D.)[1]} |
| Room Temp. | 2.51 | — | — | 2.58 | 2.44 | 2.31 | 2.20 |
|  | (0.21) |  |  | (0.26) | (0.31) | (0.13) | (0.23) |
| 37° C. | 2.88 | — | 2.95 | 2.39 | 2.33 | 2.22 | 2.07 |
|  | (0.21) |  | (0.20) | (0.15) | (0.17) | (0.12) | (0.11) |
| 45° C. | 2.74 | 2.61 | 2.50 | 2.31 | 1.92 | 2.05 | 2.01 |
|  | (0.33) | (0.22) | (0.16) | (0.15) | (0.25) | (0.31) | (0.11) |

[1]Mean ± Standard Deviation (N = 3).
[2]Permeation rate of triplicate sample dosage units determined using 5–7 week old female hairless mouse skin in Chien et al. procedure for 146 hours and the rates determined from slope of Q vs permeation time plots.

EXAMPLE 9

The procedure of Example 8 is followed to provide other transdermal dosage units of this invention: 1) 17-betaestradiol in combination with norethindrone or norgestimate, 2) ethinyl estradiol-norgestimate combination, and 3) the other combinations with progestins and estrogens selected from those named above, with the skin permeation rates necessary to provide the desired daily dose for fertility control or estradiol replacement. Also, the above dosage units of this Example and Example 8 are repeated using the other adhesives and polymers named above.

What is claimed is:

1. A transdermal estrogen/progestin dosage unit comprising:
   (a) a backing layer which is substantially impervious to the estrogen and progestin hormones to be delivered transdermally;
   (b) a polymer layer which is adhered to said backing layer and which has dissolved and/or microdispersed therein an effective dosage amount of one or more effective estrogens absorbable transdermally and are pharmaceutically acceptable, said polymer being bioacceptable, providing a compatible enviroment for said one or more estrogens and permitting said one or more estrogens to be transmitted for transdermal absorption, and
   (c) an adhesive layer in intimate contact with said polymer layer, said adhesive layer having dissolved and/or microdispersed therein an effective dosage amount of one or more effective progestins, which are absorbable transdermally and are pharmaceutically acceptable, said adhesive layer being bioacceptable, providing a compatible enviroment for said one or more progestins, and permitting said one or more progestins and said one or more estrogens to be transmitted for transdermal absorption, said adhesive layer having an effective amount of transdermal skin absorption enhancing agent;

said hormones being stable in said polymer and adhesive layers and being transdermally absorbed simultaneously to provide at least minimum effective daily doses of said hormones to effect fertility control or estrogen replacement therapy.

2. A transdermal dosage unit of claim 1 which has ethinyl estradiol or 17-beta-estradiol or combinations thereof as said one or more estrogens.

3. A transdermal dosage unit of claim 1 which has norethindrone or norgestimate or combinations thereof as said one or more progestins.

4. A transdermal dosage unit of claim 1 which has ethinyl estradiol as said estrogen and norethindrone or norgestimate as said progestin.

5. A transdermal dosage unit of claim 1 which has 17-beta-estradiol as said estrogen and norethindrone or norgestimate as said progestin.

6. A transdermal dosage unit of claim 1 in which said adhesive layer or said polymer layers or both layers are made from a polyacrylic adhesive polymer.

7. A transdermal dosage unit of claim 6 in which said polyacrylic adhesive polymer has the following formula:

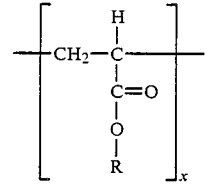

wherein x represents the number of repeating units sufficient to provide the defined properties of said adhesive layer or polymer layer or both layers and R is selected from H or lower alkyl.

8. A transdermal dosage unit of claim 1 in which the backing layer is microporous and breathable.

9. A transdermal dosage unit of claim 1 in which said adhesive layer or polymer layer or both layers are made from a silicone adhesive polymer or a polyisobutylene adhesive polymer.

10. A transdermal dosage unit of claim 1 in which the Enhancing Factor with regard to said progestin is at least 1.2, 1.3, 1.5 or 2.0.

11. A transdermal dosage unit of claim 1 wherein the transdermal skin absorption enhancing agent is n-decyl alcohol.

12. A transdermal dosage unit of claim 1 which effectively provides at least minimum daily dosage amounts of said estrogen and progestin for about one week, having an amount of said skin permeation absorption enhancing agent to provide an Enhancing Factor of at least about 1.5 with regard to said progestin.

13. A transdermal dosage unit of claim 1 wherein said polymer layer having present one or more estrogens and said adhesive layer having present one or more progestins are separated by, but are in respective intimate contact therewith, a bioacceptable adhesive or polymer separating layer through which said one or more estrogens are transmitted for desired transdermal absorption, said separating layer made using an adhesive or polymer which is free or substantially free of estrogen, progestin and enhancing agents.

14. A transdermal dosage unit of claim 13 which has ethinyl estradiol or 17-beta-estradiol or combinations thereof as said one or more estrogens and norethindrone or norgestimate or combinations thereof as said one or more progestins.

15. A transdermal dosage unit of claim 13 wherein the separating layer is made from a bioacceptable adhesive or polymer having a sufficiently high viscosity or molecular weight to provide a dimensionally stable separating layer and a substantial reduction in the transmission rate of said one or more estrogens.

16. A transdermal dosage unit of claim 15 where the separating layer is made from a polyisobutylene adhesive.

17. A transdermal dosage unit of claim 15 wherein the ratio of transdermally absorbed progestin to estrogen hormones is in the range of about 10/1 to about 30/1.

18. A transdermal dosage unit of claim 17 wherein the ratio of transdermally absorbed progestin to estrogen hormones is in the range of about 12/1 to about 20/1.

19. A transdermal dosage unit of claim 17 wherein the separating layer is made from polyisobutylene.

20. A transdermal dosage unit of claim 18 wherein the separating layer is made from polyisobutylene having a relative molecular mass $M_V$ (viscosity average) of from about 800,000 to about 900,000.

21. A transdermal dosage unit of claim 17 which has ethinyl estradiol or 17-beta-estradiol or combinations thereof as said one or more estrogens and has norethindrone or norgestimate or combinations thereof as said one or more progestins.

22. A transdermal dosage unit of claim 21 wherein the adhesive or polymer is a bioacceptable polyisobutylene.

23. A transdermal dosage unit of claim 22 where the separating layer has a thickness of from about 75 to about 125 microns and the polyisobutylene has a relative molecular mass $M_V$ (viscosity average) of at least about 800,000.

* * * * *